US006938619B1

(12) United States Patent
Hickle

(10) Patent No.: US 6,938,619 B1
(45) Date of Patent: Sep. 6, 2005

(54) MASK FREE DELIVERY OF OXYGEN AND VENTILATORY MONITORING

(75) Inventor: Randall S. Hickle, Lubbock, TX (US)

(73) Assignee: Scott Laboratories, Inc., Lubbock, TX (US)

( * ) Notice: Subject to any disclaimer, the term of this patent is extended or adjusted under 35 U.S.C. 154(b) by 416 days.

(21) Appl. No.: 09/592,943

(22) Filed: Jun. 13, 2000

(51) Int. Cl.[7] ............................................. A61M 15/08
(52) U.S. Cl. ........................... 128/207.18; 128/207.14; 128/203.22; 128/204.18; 128/204.22; 128/204.23; 128/204.26
(58) Field of Search ....................... 128/204.18, 204.22, 128/204.23, 205.25, 207.18, 207.14, 200.24, 201.18, 202.22, 203.22, 204.26; 482/13; 600/538, 539, 543

(56) References Cited

U.S. PATENT DOCUMENTS

| 4,141,353 | A |   | 2/1979  | Dahlback et al. | 128/142 R |
| 4,151,843 | A |   | 5/1979  | Brekke et al.   | 128/203   |
| 4,263,908 | A | * | 4/1981  | Mizerak         | 128/205.25|
| 4,550,726 | A |   | 11/1985 | McEwen          | 128/202.22|
| 4,612,928 | A |   | 9/1986  | Tiep et al.     | 128/204.23|

(Continued)

FOREIGN PATENT DOCUMENTS

EP    0 933 094 A2    4/1999
EP    0 951 918 A2    10/1999
WO    97/05824        2/1997

OTHER PUBLICATIONS

International Search Report, Application No. PCT/US01/18891 dated May 22, 2002.

Oridion; 3.0 510(K) Summary Of Safety And Effectiveness Information; Oridion Medical Ltd.

*Primary Examiner*—Glenn K. Dawson
*Assistant Examiner*—Darwin P Erezo
(74) *Attorney, Agent, or Firm*—Hogan & Hartson, LLP

(57) ABSTRACT

Disclosed is an apparatus and method for the delivery of supplemental oxygen gas to a person combined with the monitoring of the ventilation of the person with both being accomplished without the use of a sealed face mask. Preferred embodiments of the present invention combine an oxygen delivery device, a nasal airway pressure sampling device, an oral airway pressure sampling device, and a pressure analyzer connected to the sampling devices to determine the phase of the person's respiration cycle and the person's primary airway. The oxygen delivery device is connected to a controller such that it delivers a higher flow of oxygen to the person during the inhalation phase of the person's respiratory cycle. The invention thus increases end tidal oxygen concentrations with improved efficiency comparative to known open airway devices. Embodiments of the invention can include carbon dioxide sampling tubes that continuously sample air from the nose and mouth to determine carbon dioxide concentration during exhalation.

49 Claims, 8 Drawing Sheets

U.S. PATENT DOCUMENTS

| | | | |
|---|---|---|---|
| 4,618,099 A | 10/1986 | Nagao et al. | 239/332 |
| 4,686,974 A | 8/1987 | Sato et al. | 128/204.23 |
| 4,686,975 A | 8/1987 | Naimon et al. | 128/204.23 |
| 4,728,110 A | 3/1988 | Nakasone | 277/213 |
| 4,924,876 A | 5/1990 | Cameron | 128/725 |
| 5,003,985 A | 4/1991 | White et al. | 128/716 |
| 5,005,571 A * | 4/1991 | Dietz | 128/205.25 |
| 5,046,491 A | 9/1991 | Derrick | 128/200.24 |
| 5,050,614 A | 9/1991 | Logan | 128/716 |
| 5,050,615 A | 9/1991 | Malkamaki | 128/719 |
| 5,074,299 A | 12/1991 | Dietz | 128/204.21 |
| 5,099,836 A | 3/1992 | Rowland et al. | 128/204.23 |
| 5,253,640 A | 10/1993 | Falb et al. | 128/200.24 |
| 5,365,922 A | 11/1994 | Raemer | 128/204.23 |
| 5,386,833 A | 2/1995 | Uhen | 128/719 |
| 5,402,796 A * | 4/1995 | Packer et al. | 128/719 |
| 5,433,195 A * | 7/1995 | Kee et al. | 128/207.14 |
| 5,474,060 A | 12/1995 | Evans | 128/204.22 |
| 5,485,850 A | 1/1996 | Dietz | 128/716 |
| 5,509,414 A * | 4/1996 | Hok | 128/660.02 |
| 5,622,164 A | 4/1997 | Kilis et al. | 128/200.24 |
| 5,694,923 A * | 12/1997 | Hete et al. | 128/204.18 |
| 5,735,268 A * | 4/1998 | Chua et al. | 128/204.23 |
| 5,800,361 A | 9/1998 | Rayburn | 600/532 |
| 5,803,065 A * | 9/1998 | Zdrojkowski et al. | 128/204.23 |
| 5,865,174 A | 2/1999 | Kloeppel | 128/204.23 |
| 6,017,315 A | 1/2000 | Starr et al. | 600/538 |
| 6,095,139 A * | 8/2000 | Psaros | 128/204.22 |
| 6,155,986 A * | 12/2000 | Brydon et al. | 600/538 |
| 6,186,142 B1 | 2/2001 | Schmidt et al. | 128/204.23 |
| 6,192,884 B1 | 2/2001 | Vann et al. | 128/204.26 |
| 6,213,955 B1 * | 4/2001 | Karakasoglu et al. | 600/529 |
| 6,247,470 B1 * | 6/2001 | Ketchedjian | 128/200.28 |
| 6,379,312 B2 * | 4/2002 | O'Toole | 600/529 |
| 6,401,713 B1 * | 6/2002 | Hill et al. | 128/204.21 |
| 6,422,240 B1 * | 7/2002 | Levitsky et al. | 128/207.18 |
| 6,532,958 B1 * | 3/2003 | Buan et al. | 128/204.23 |

* cited by examiner

MASK FREE DELIVERY OF OXYGEN AND VENTILATORY MONITORING

BACKGROUND OF THE INVENTION

1. Field of the Invention

The invention relates to an apparatus and method for the delivery of supplemental oxygen gas to a person combined with the monitoring of the ventilation of the person, and more particularly to an apparatus and method where such delivery of oxygen and monitoring of ventilation is accomplished without the use of a sealed face mask.

2. Description of Related Art

In various medical procedures and treatments performed on patients, there is a need to deliver supplemental oxygen ($O_2$) gas to the patient. In procedures involving the delivery of anesthesia or where a patient is otherwise unconscious and ventilated, the delivery of oxygen (and other gaseous drugs) is typically accomplished via a mask that fits over the patient's nose and mouth and is sealed thereto or by a tracheal tube. In other procedures, however, for example, where a patient may be sedated, but conscious and breathing on their own, the delivery of supplemental oxygen gas may be accomplished via a mask or by nasal cannulae (tubes placed up each nares of a patient's nose), connected to a supply of oxygen.

The primary goal of oxygen supplementation (whether mask-free or otherwise) is to enrich the oxygen concentration of the alveoli gas, namely, the mixture of gas in the alveoli (microscopically tiny clusters of air-filled sacs) in the lungs. In a person with normal lung function, the level of oxygen in the deepest portion of the alveolar sacs is essentially reflected at the end of each "tidal volume" of exhaled gas (the volume of gas in one complete exhalation). The gas sample measured at the end of a person's exhalation is called the "end-tidal" oxygen sample.

So, for example, if a person breathes room air, room air contains 21% oxygen. When the person exhales, the end tidal gas will have about 15% oxygen; the capillary blood has thus removed 6% of the oxygen from the inhaled gas in the alveoli, to be burned by the body in the process of metabolism. Again, a simple goal of any form of oxygen supplementation is to increase the concentration of oxygen in the alveolar sacs. A convenient method of directly measuring or sampling the gas in alveolar sacs is by continuously sampling the exhaled gas at the mouth or nose and identifying the concentration of oxygen at the end-tidal point, a value that is reasonably reflective of the oxygen concentration in the alveolar sacs. Thus, one can compare the effectiveness of oxygen delivery systems by the amount that they increase the end tidal oxygen concentration.

If a person breathes through a sealing face mask attached to one-way valves and inhales a supply of 100% oxygen, the end tidal concentration of oxygen goes up to 90%. More specifically, once inert nitrogen gas has been eliminated from the lungs (after pure oxygen has been breathed for several minutes), alveolar gas will contain about 4% water vapor and 5% carbon dioxide. The remainder (about 90%) will be oxygen. Thus, the best oxygen delivery systems typically increase end tidal oxygen from a baseline of 15%, when breathing non-supplemented room air, to 90% when breathing pure oxygen. Although sealed face-masks are relatively effective oxygen delivery systems, conscious patients, even when sedated, often find masks significantly uncomfortable; masks inhibit the ability of a patient to speak and cause anxiety in patients.

Nasal cannulae, on the other hand, do not typically cause the level of discomfort or anxiety in conscious patients that masks do, and thus, from a patient comfort standpoint, are preferable over masks for the delivery of oxygen to conscious patients. Nasal cannulae are, however, significantly less effective oxygen delivery systems than sealed face masks. Nasal cannulae generally increase the end tidal oxygen concentration to about 40% (as compared to 90% for a sealed mask). Nasal cannulae are less effective for at least two reasons.

First, when a person inhales, they frequently breathe through both nasal passages and the mouth (three orifices). Thus, the weighted average concentration of inhaled oxygen is substantially diluted to the extent of mouth breathing because 21% times the volume of air breathed through the mouth "weights down the weighted average".

Second, even if a person breathes only through their nose, the rate of inhalation significantly exceeds the supply rate of the nasal cannula (typically 25 liters/min.) so the person still dilutes the inhaled oxygen with a supply of 21% room air. If the nasal cannula is flowing at 2 liters per minute and a person is inhaling a liter of air over 2 seconds, the inhalation rate is 60 liters per minute, and thus, most of the inhaled volume is not coming from the nasal cannula, but rather from the room. Increasing the oxygen flow rate does not effectively solve this problem. First, patients find increased flow very uncomfortable. Second, increased oxygen flow dilutes (washes away) the exhaled carbon dioxide, then carbon dioxde cannot be sampled as a measure of respiratory sufficiency.

There is also a need in various medical procedures and treatments to monitor patient physiological conditions such as patient ventilation (the movement of air into and out of the lungs, typically measured as a volume of air per minute). If the patient does not move air into and out of the lungs then the patient will develop oxygen deficiency (hypoxia), which if severe and progressive is a lethal condition. Noninvasive monitoring of hypoxia is now available via pulse oximetry. However, pulse oximetry may be late to diagnose an impending problem because once the condition of low blood oxygen is detected, the problem already exists. Hypoventilation is frequently the cause of hypoxemia. When this is the case, hypoventilation can precede hypoxemia by several minutes. A good monitor of ventilation should be able to keep a patient "out of trouble" (if the condition of hypoventilation is diagnoses early and corrected) whereas a pulse oximeter often only diagnosed that a patient is now "in" trouble. This pulse oximetry delay compared to ventilatory monitoring is especially important in acute settings where respiratory depressant drugs are administered to the patient, as is usually the case during painful procedures performed under conscious sedation.

Ventilatory monitoring is typically measured in terms of the total volumetric flow into and out of a patient's lungs. One method of effective ventilatory monitoring is to count respiratory rate and then to measure one of the primary effects of ventilation (removing carbon dioxide from the body).

There are a variety of ventilation monitors such as 1) airway flowmeters and 2) capnometers (carbon dioxide detectors). These monitors are used routinely for patients undergoing general anesthesia. These types of monitors work well when the patient's airway is "closed" in an airway system such as when the patient has a sealing face mask or has the airway sealed with a tracheal tube placed into the lungs. However, these systems work less well with an "open" airway such as when nasal cannulae are applied for oxygen supplementation. Thus, when a patient has a non-sealed airway, the options for tidal volume monitoring are limited. With an open airway, there have been attempts to monitor ventilation using capnometry, impedance plethysmography, and respiratory rate derived from the pulse oximeter's plethysmogram. The limitations of each are discussed below.

Nasal capnometry is the technique of placing a sampling tube into one of the nostrils and continuously analyzing the carbon dioxide content present in the airstream thereof. Nasal capnometry is relatively effective provided that 1) the patient always breathes through his/her nose, and 2) nasal oxygen is not applied. More specifically, if the patient is talking, most of the exhalation is via the mouth, and frequent false positive alarms sound because the capnometer interprets the absence of carbon dioxide in the nose as apnea, when in fact, it is merely evidence of talking. A couple of devices in the prior art have tried to overcome this problem by: manual control of sampling from the nose or mouth (Nazorcap); supplementing oxygen outside of the nose while sampling for $CO_2$ up inside the nose (BCI); providing oxygen in the nose while sampling $CO_2$ from the mouth (BCI); and supplying oxygen up one nostril and sampling for $CO_2$ Up inside the other nostril (Salter Labs). None of these already-existing systems provide oxygen to both the nose and mouth or allow automatic control of sampling from either site. Further, if nasal oxygen is applied to the patient, the carbon dioxide in each exhalation can be diluted significantly by the oxygen supply. In this case, the capnometer may interpret the diluted $CO_2$ sample as apnea (stoppage in breathing), resulting once again, in frequent false positive alarms.

Impedance plethysmography and plethysmogram respiratory rate counting also suffer drawbacks as primary respiratory monitors. Impedance plethysmography is done via the application of a small voltage across two ECG electrode pads placed on each side of the thoracic cage. In theory, each respiration could be detected as the phasic change of thoracic impedance. Unfortunately, the resulting signal often has too much noise/artifact which can adversely effect reliability. Respiratory rate derived from the pulse oximeter's plethysmogram may not diagnose apnea and distinguish it from complete airway obstruction, thus misdiagnosing apnea as a normal condition (a false negative alarm state).

In view of the above drawbacks to current systems for delivering supplemental oxygen gas and monitoring ventilation, there is a need for an improved combined system to accomplish these functions.

SUMMARY OF THE INVENTION

One of the purposes of the current invention is to increase the alveolar oxygen concentration without the requirement for a patient to wear a mask.

This is done by:

1) Delivering a higher flow of oxygen (e.g. 10–15 liters per minute)
2) Making this higher flow of oxygen acceptable to patients by providing it only during the inhalation part of the respiratory cycle (so the patient does not get a continuous sensation of high flow oxygen)
3) Making the higher flow of oxygen acceptable to the patient by opening a variable orifice for oxygen supply slowly rather than going to immediate full-open or otherwise diffusing the oxygen supply, which minimizes the sensation of a rapid burst of oxygen beginning with each inhalation.
4) Providing oxygen flow to all three respiratory orifices (i.e., provide flow over both nostrils and the mouth) during the inhalation cycle. Thus, inhaled gas is not diluted at any inhalation portal by pure room air.
5) The supply source for oxygen is a multiplicity of holes rather than single lumen cannula. This decreases the Bernoulli-effect of air entrainment that occurs when a high velocity of gas is delivered through a single cannula.

The invention thus increases end tidal oxygen concentrations from the baseline 15% (breathing room air) up to 50–55%. Whereas this is not as effective as face mask oxygen supplementation, it is significantly better than the prior art for open airway oxygen supplementation devices.

A second purpose of the invention is to more effectively monitor patient ventilation in combination with mask-free delivery of oxygen gas to the patient.

In this aspect, the invention includes placing pressure lumens inside one of a patient's nostrils and in front of the patient's mouth. The pressure lumens are connected to pressure transducers which in turn are connected to a processor running software. A carbon dioxide sampling tube accompanies each pressure lumen. The nasal and mouth pressure samples from the respective lumens are continually compared with one another to determine the primary ventilatory path i.e., whether the nose or mouth is the primary respiratory site. That is, whichever orifice is experiencing greater pressure swings is selected as the location of the primary ventilatory path. The carbon dioxide sampling tubes continuously sample gas from the nose and mouth and are connected to a solenoid valve which is in turn connected to a capnometer. Once the comparators (pressure transducers) determine the primary ventilatory path, the solenoid valve is opened so that only the sample from the primary path is run to the capnometer.

The software also analyzes the pressures sampled from each orifice to determine whether the patient is inhaling or exhaling. The software opens a solenoid valve connected to an oxygen source so that oxygen flow is high only during the inhalation phase of the patient's breathing.

In addition to being connected to pressure transducers, each pressure lumen is also connected to a microphone that amplifies the patient's respiratory sounds so they may be heard by a care giver in the room.

DESCRIPTION OF PREFERRED EMBODIMENTS

Figure 1:
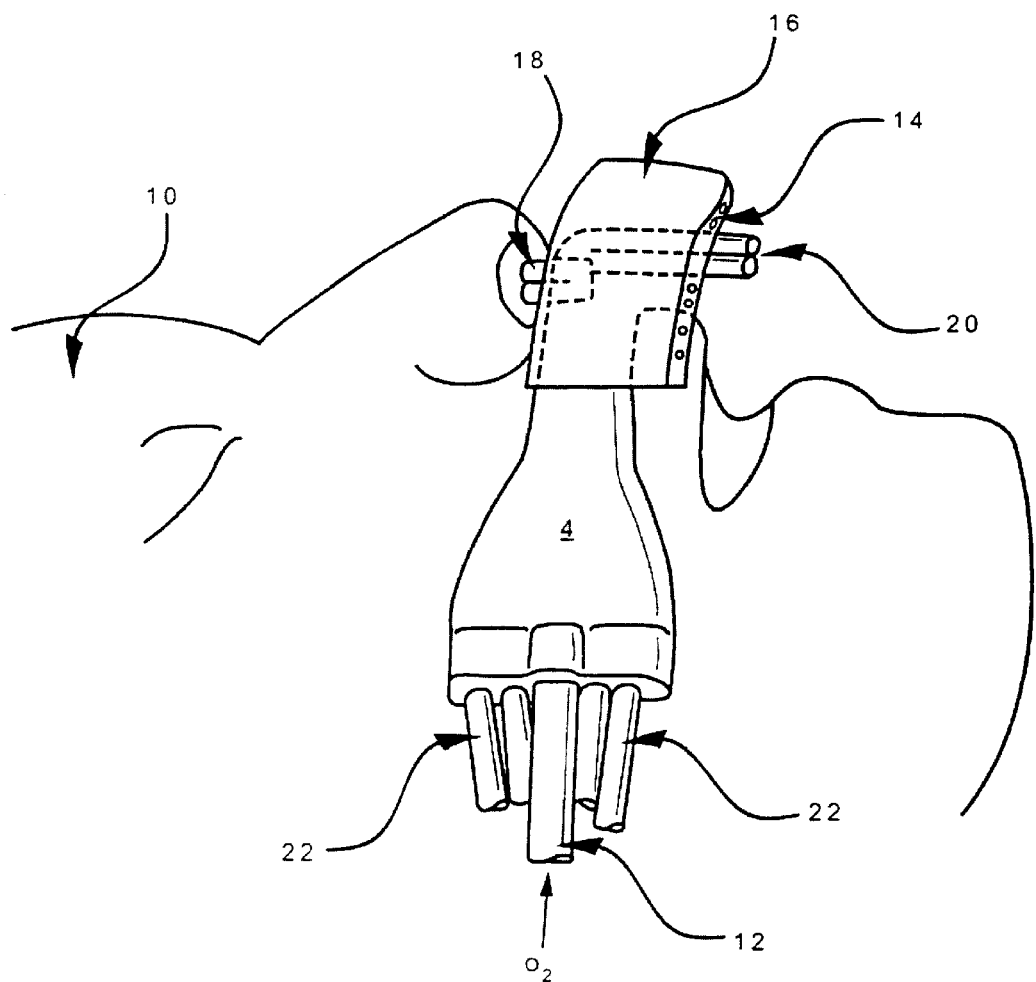
FIG. 1 shows a side, cut out view of the disposable portion of the apparatus placed on a patient in accordance with the invention.

FIG. 1 shows a cut-out view of the disposable portion 4 of an apparatus in accordance with the invention placed on a patient 10.

The apparatus provides for the mask-free delivery of supplemental oxygen gas to the patient combined with the monitoring of patient ventilation. Oxygen gas is supplied to the patient from an $O_2$ supply tube 12 and exits portion 4 from a diffuser grid 14 in housing 16 (shown in more detail in FIG. 2). Diffuser grid 14 blows diffused oxygen into the immediate area of the patient's nose and mouth. Two thin lumens (tubes) are mounted adjacent one another to portion 4 and placed in one of the patient's nostrils (nasal lumens 18). Another two thin lumens are also mounted adjacent to one another to portion 4 placed in front of the patient's mouth (oral lumen's 20).

Of nasal lumens 18, one lumen is a pressure lumen for sampling the pressure resulting from a patient's nose breathing and the other lumen continuously samples the respiratory gases so they may be analyzed in the capnometer to determine the concentration of carbon dioxide. This arrangement is essentially the same for oral lumens 20, namely, one lumen is a pressure lumen (samples pressure in mouth breathing) and the other lumen continuously samples the respiratory gases involved in mouth breathing. Nasal lumens 18 and oral lumens 20 are each connected to their own pneumatic tubes, e.g., 22, which feed back the nasal and oral pressure samples to pressure transducers (not shown) and which feed back the nasal and oral gas samples to a capnometer (not shown). All of portion 4; lumens 18, 20; oxygen supply tubing 12 and feedback tubing 22 are disposable (designed to be discarded after every patient use), and preferably constructed of pliable plastic material such as extruded poly-vinyl chloride.

Figure 2:
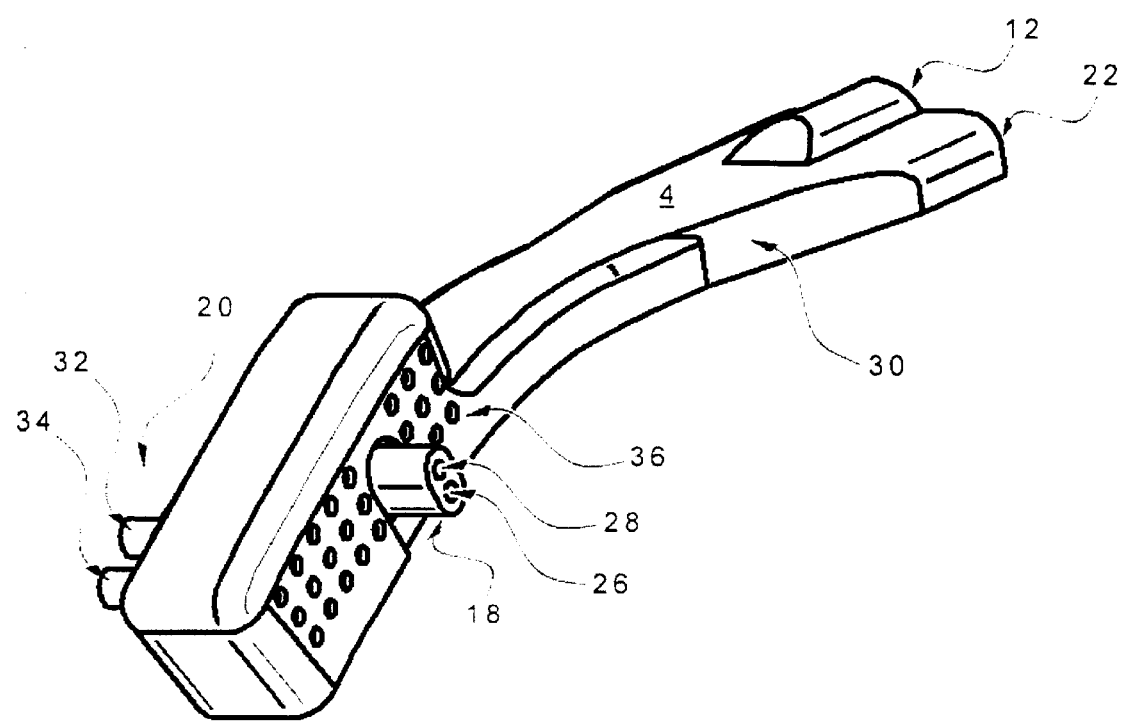
FIG. 2 shows a perspective exterior view of the disposable portion of the apparatus in accordance with the invention.

As shown in FIG. 2, lumens 18, 20 and tubings 12 and 22, although shown as a portion cut-out in FIG. 1 in a preferred embodiment, are housed in cover 30. Also, in FIG. 2, nasal lumens 18 (including pressure lumen 28 and $CO_2$ lumen 26) are formed from a double-holed, single-barrel piece. Oral lumens 20 (which include pressure lumen 32 and $CO_2$ lumen 34) are preferably formed from a double barrel piece. Diffuser grid 36 is formed in cover 30 and functions as an oxygen diffuser which releases a cloud of oxygen into the immediate oral and nasal area of the patient 10.

Figure 3:
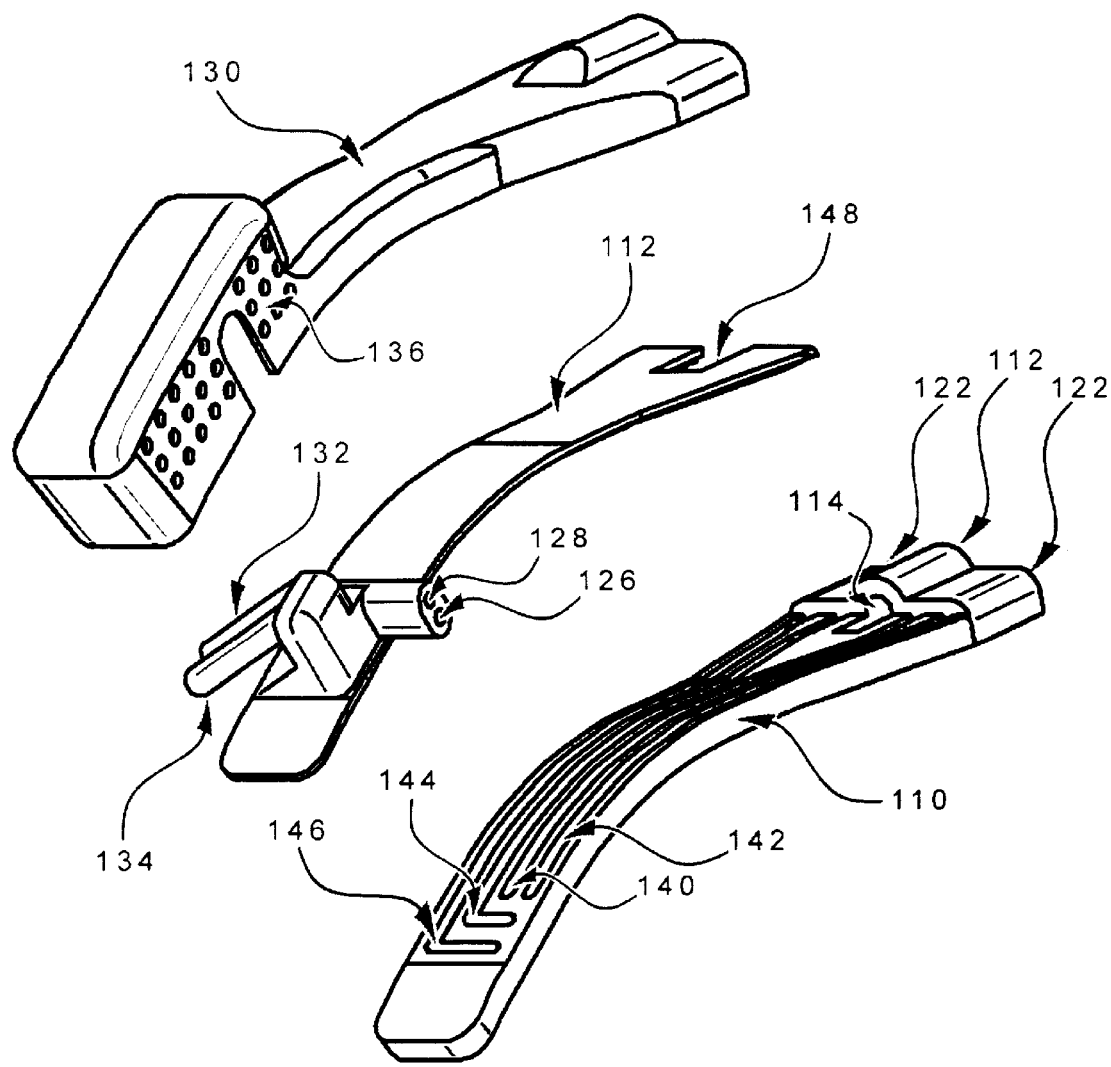
FIG. 3 is a blow-up view showing the lower, middle and cover portions of the disposable portion of the apparatus in accordance with the invention.

FIG. 3 shows disposable portion 4 including cover 30 in more detail in cut-out fashion. Specifically, lower portion 110, formed from a suitably firm, but not rigid, plastic, has an opening 112 for insertion of oxygen supply tube 12. Slot 114 in portion 110 receives the oxygen gas from the tube 12, retains it, and forces it up through opening 148 in middle portion 112. Middle portion 112 is affixed to lower portion 110 lying flat on portion 110. From opening 148, the oxygen gas travels into cover 130 (affixed directly onto middle portion 112) and travels lengthwise within cover 130 to diffuser portion 135, whereupon the oxygen exits cover 130 through diffuser grid 136 into the immediate vicinity of the patient's nose and mouth in a cloud-like fashion. It is preferable to supply oxygen flow to all three respiratory orifices (both nostrils and mouth) to increase the concentration of oxygen provided to the patient. By providing flow to all three orifices inhaled gas is not diluted at any inhalation portal by pure room air. Also, a diffused stream such as that created by grid 136 is a preferred embodiment for the oxygen stream delivered to the patient. This is because a stream of oxygen delivered through a single lumen cannula is typically uncomfortable at the higher flow rates necessary for sufficient oxygen delivery. Further, at those flow rates, a single lumen can create an undesirable Bernoulli effect. It is noted that an alternative to the diffuser grid 136 is a cup-shaped or other chamber which receives the $O_2$ jet-stream and includes a foam or filler paper section for diffusing the jet stream of $O_2$.

As is also shown in FIG. 3, feedback tubing 22 enters lower portion 110 at openings 122. At one opening 122 begin grooves 146 and 140 formed in lower portion 110 each for receiving the feedback pressure sample from lumens 128 and 132. At the other opening 122 begin groves 144 and 142, formed in lower portion 110 each for receiving the feedback $CO_2$ sample from lumens 126 and 134. Grooves 146, 144, 140 and 142, all formed in lower portion 110, connect at one end to their respective sampling lumens (128, 126, 132 and 134) and at their other end to feedback tubing 22; middle portion 112 lies flat on and affixed to portion 110 such that the grooves 146, 144, 140 and 142 form passageways for the respective feedback samples. As can be seen, when assembled portions 130, 112 and 110 together form whole disposable piece 4, shown perceptively in FIG. 2.

Figure 4:
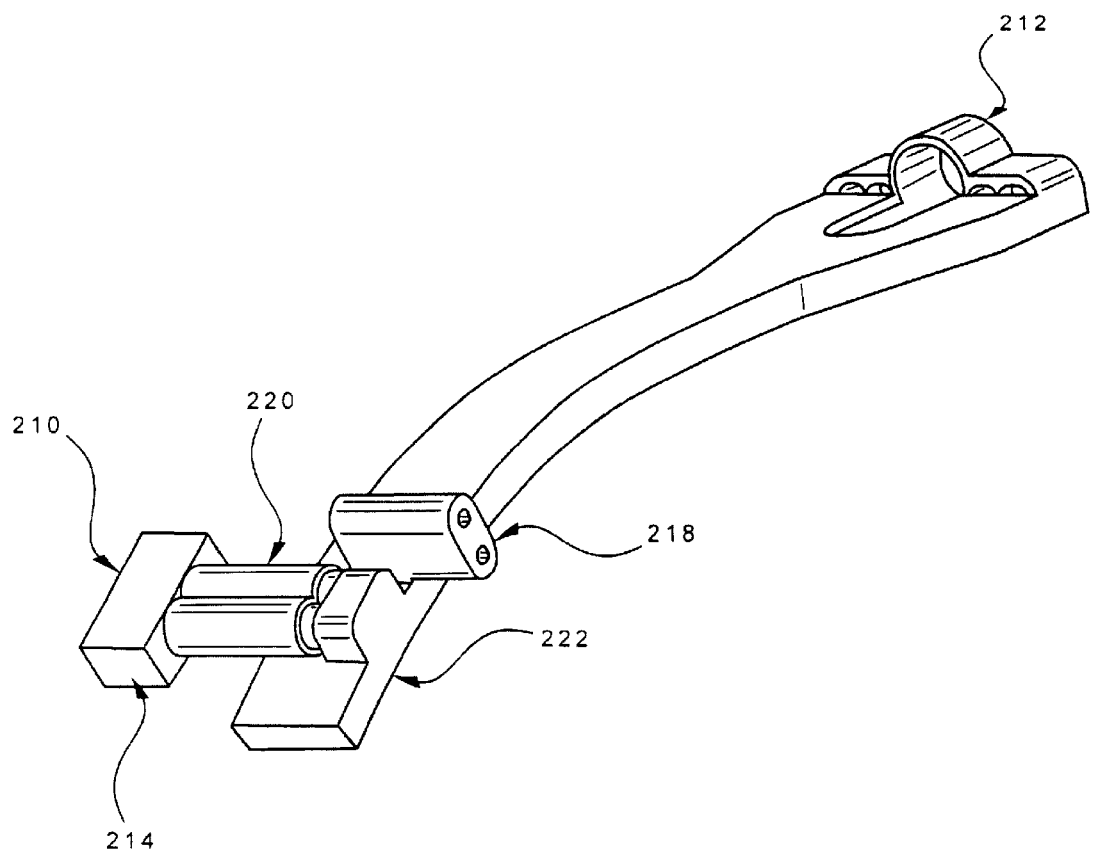
FIG. 4 shows an embodiment of the disposable portion of the apparatus with an oral collection chamber in accord with the invention.

FIG. 4 shows a preferred embodiment of disposable portion 4 (here portions 110 and 112 are shown affixed to one another) with an oral sample collection chamber 210 fitting over oral lumens 220 (nasal lumens are shown) at 218 and the opening for the oxygen supply tube is shown at 212). Oral sample collector 210 is preferably constructed of plastic and creates a space in chamber 214 that collects a small volume of air the patient has breathed orally. That volume of air is then sampled by lumens 220 and fed back for analysis through the respective pressure and $CO_2$ feedback tubing to pressure transducers and the capnometer described above. Collector 210 thus acts as a storage container for better sampling of the oral site. It also serves as a capacitor for better monitoring of oral site pressure (exhalation contributes to volume and pressure increases, while inhalation removes air molecules from volume and pressure decreases).

In one preferred embodiment, collector 210 is provided in a variety of sizes and shapes to collect different volumes of air or to facilitate different medical procedures which may be performed in or near the mouth. In another preferred embodiment collector 210 is adjustable in that it is capable of sliding over lumens 220 to enable positioning directly over the mouth's airstream. In a further embodiment, lumens 220 are themselves also slidably mounted to portion 222 so as to be extendable and retractable to enable positioning of both the lumens and collector directly in front of the oral airstream.

Figure 5A:
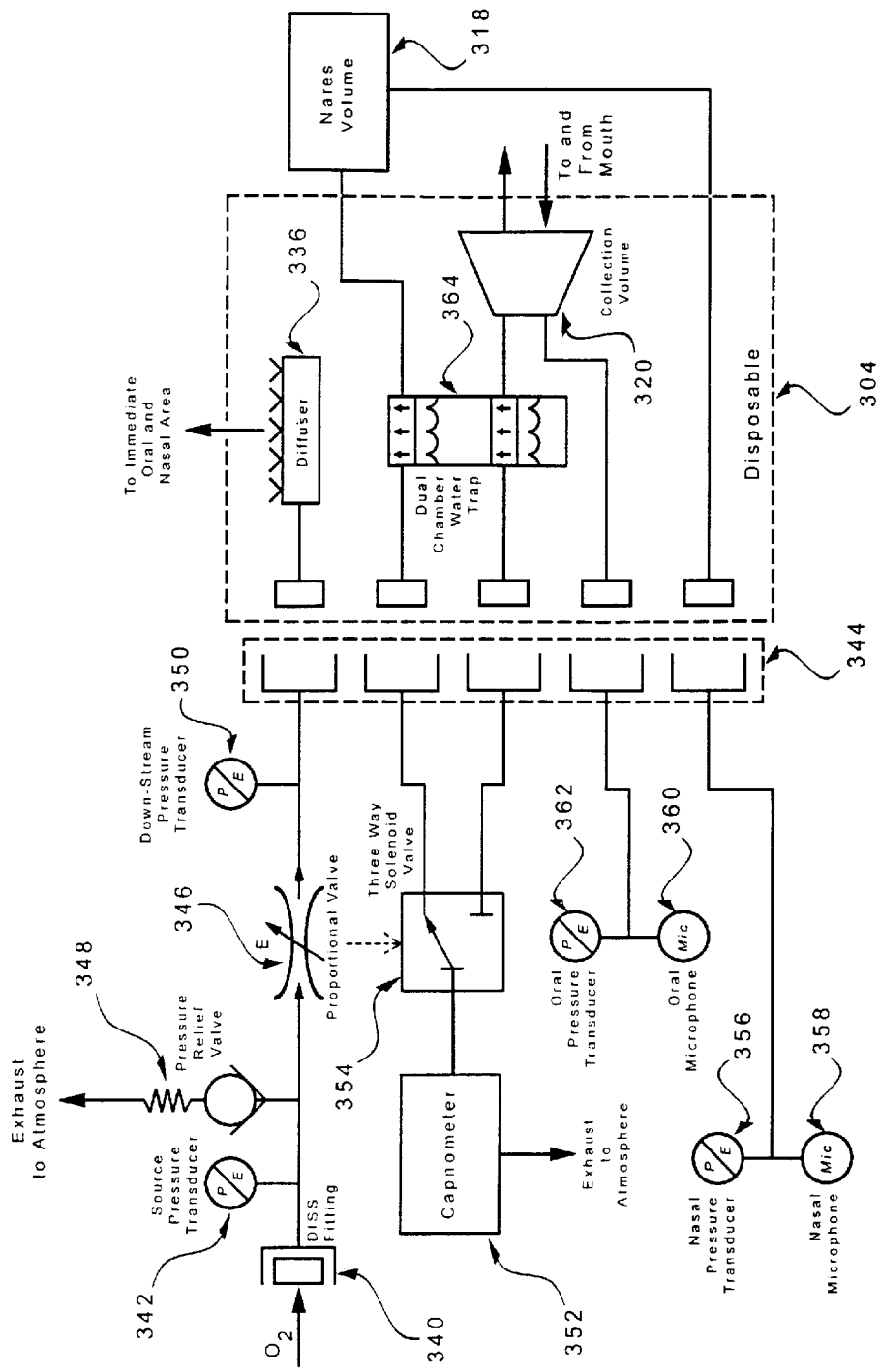
FIG. 5A is a schematic diagram of an oxygen delivery and ventilatory monitoring system in accordance with one embodiment of the invention.

FIG. 5A shows a schematic circuit diagram of a preferred embodiment of the oxygen delivery and ventilatory monitoring system of the invention. As described above, disposable portion 304 includes nasal lumens which sample a nasal (nares) volume 318 of air breathed through the patient's nostril; an oral sample collector which creates an oral volume of air 320 effecting sampling of air breathed through a patient's mouth; and an oxygen diffuser 336 which enriches the immediate breathing area of a patient with oxygen, increasing the patient's fraction of inspired oxygen and thereby increasing the patient's alveolar oxygen levels. The diffuser 336 ensures that a high rate of oxygen flow is not uncomfortable for the patient.

Oxygen gas is supplied to diffuser 336 from an oxygen supply ($O_2$ tank or in-house oxygen). If the supply of $O_2$ is from an in-house wall source, DISS fitting 340 is employed. The DISS fitting 340 (male body adaptor) has a diameter indexed to only accept Compressed Gas Association standard oxygen female nut and nipple fitting. A source pressure transducer 342 monitors the oxygen source pressure and allows software running on processor 344 to adjust the analog input signal sent to proportional valve 346 in order to maintain a user-selected flow rate as source pressure fluctuates. Pressure relief valve 348 relieves pressure to the atmosphere if the source pressure exceeds 75 psi. Proportional valve 346 sets the flow rate of oxygen (e.g. 2.0 to 15.0 liters per minute) through an analog signal and associated driver circuitry (such circuitry is essentially a voltage to current converter which takes the analog signal to a dictated current to be applied to the valve 346, essentially changing the input signal to the valve in proportion to the source pressure, as indicated above). Downstream pressure transducer 350 monitors the functionality of proportional valve 348. Associated software running on processor 344 indicates an error in the delivery system if source pressure is present, the valve is activated, but no downstream pressure is sensed.

As described above, the nares volume 318 and oral collection volume 320 are fed back to the capnometer 352 via a three-way solenoid valve 354. The capnometer 352 receives the patient airway sample and monitors the $CO_2$ content within the sample. Software associated with capnometer 352 displays pertinent parameters (such as a continuous carbon dioxide graphic display and digital values for end-tidal $CO_2$ and respiration rate) to the user. A suitable capnometer may be that manufactured by Nihon Kohden (Sj5i2). Three-way solenoid valve 354 automatically switches the sample site between the oral site and the nasal site depending on which site the patient is primarily breathing through. This method is described in more detail below, but briefly, associated software running on processor 344 switches the sample site based on logic that determines if the patient is breathing through the nose or mouth. It is preferable to have a short distance between the capnometer and valve 354 to minimize dead space involved with switching sample sites.

Also as described above, the nares volume 318 collected is fed back to a nasal pressure transducer 356 and nasal microphone 358. Transducer 356 monitors the pressure in the nares volume 318 through the small bore tubing described above. Associated software running on processor 344 determines through transducer 356 if the patient is breathing primarily through the nose. Associated offset, gain and temperature compensation circuitry (described below) ensures signal quality. Nasal microphone 358 monitors the patient's breath sounds detected at the nasal sample site. Associated software allows the user to project sound to the room and control volume. Output from microphone 358 may be summed with output of the oral microphone 360 for a total breath sound signal. In an additional embodiment the breath sound signals are displayed to the user and/or further processed and analyzed in monitoring the patient's physiological condition.

Oral pressure transducer 362 monitors pressure at the oral collection volume 320 through the small bore tubing described above. Associated software running on processor 344 determines via monitor 362 if the patient is primarily breathing through the mouth. Offset gain and temperature compensation circuitry ensure signal quality. Oral microphone 360 operates as nasal microphone 358 described above to project breath sounds to the room.

Dual chamber water trap 364 guards against corruption of the $CO_2$ sensors by removing water from the sample volumes. Segregated chambers collect water removed by hydrophobic filters associated with the nasal and oral sites. This segregation ensures that the breathing site selected as the primary site is the only site sampled.

Figure 5B:
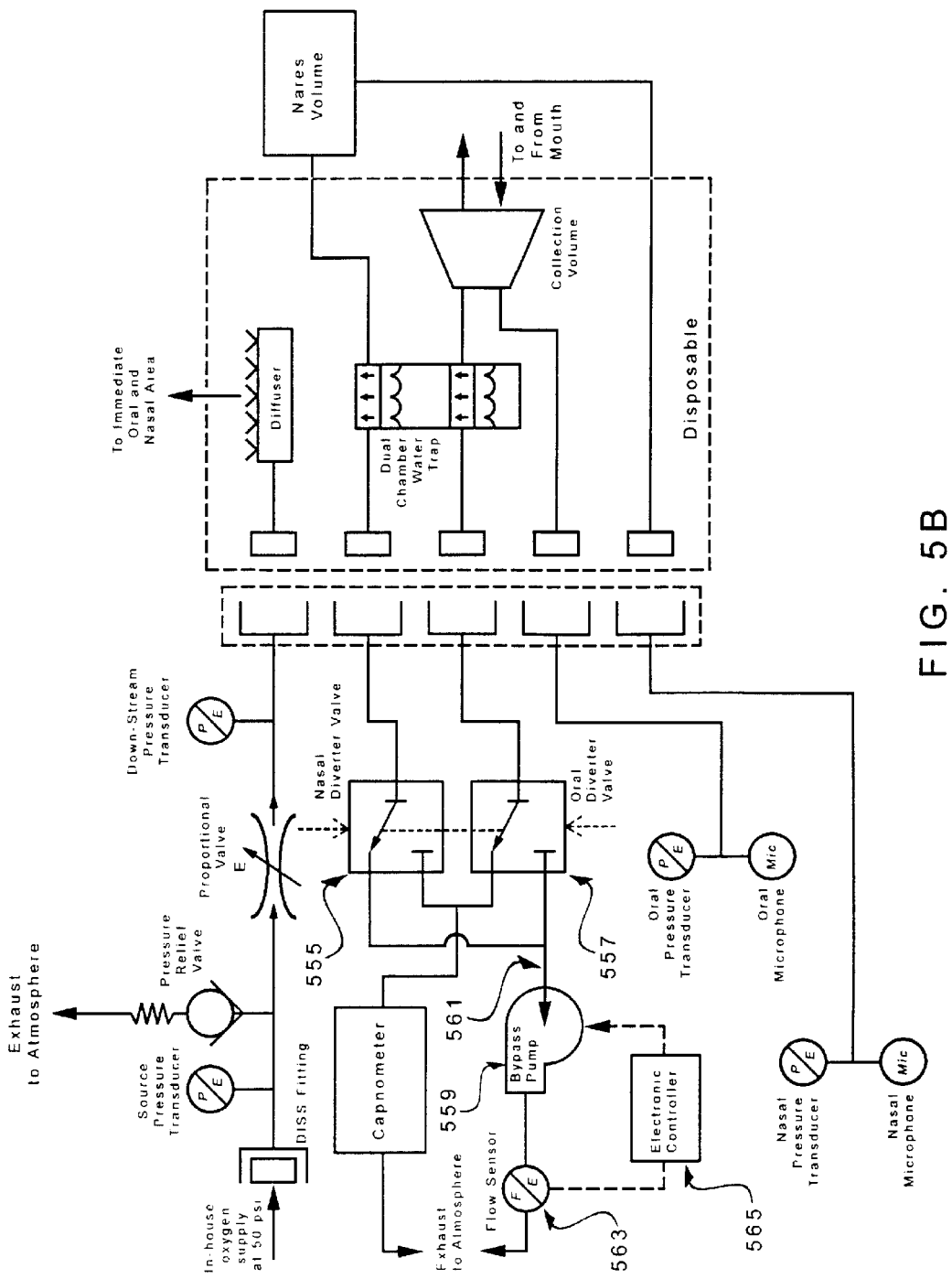
FIG. 5B is a schematic diagram of an oxygen delivery and ventilatory monitoring system in accordance with an alternative embodiment of the invention.

FIG. 5B shows an additional embodiment of the system circuit of the present invention, including a sample bypass circuit which keeps the sample sites flowing at the same rate, regardless of whether the site is being sampled by the capnometer or bypassed. Specifically, nasal diverter valve 555 switches the nasal sample between the capnometer for $CO_2$ sampling and the bypass line. Activation of the valve 555 is linked to activation of oral diverter valve 557 in order to ensure that one sample is connected to the bypass line while the other sample is connected to the capnometer. This allows two states: 1) the oral site fed back to the capnometer, with the nasal site to the bypass; and 2) the nasal site fed back to the capnometer with the oral site on bypass. As described above, the control software switches the sample site based on logic that determines if the patient is breathing through the nose or mouth. Oral diverter valve 557 switches the oral sample between the capnometer for $CO_2$ sampling and the bypass line and operates as described with respect to nasal diverter valve 555.

Bypass pump 559 maintains flow in the bypass line 561 that is equivalent to flow dictated by the capnometer (e.g., 200 cm/min.). The pump 559 also ensures that the sample sites are synchronized with one another so that the $CO_2$ waveform and respiration rate calculations are not corrupted when sample sites are switched. Flow sensor 563 measures the flow rate obtained through the bypass line 561 and provides same to electronic controller 565 necessary for flow control. Controller 565 controls the flow of pump 559.

As can be seen from FIG. 5B, balancing the flow between the active sample site and the bypass (e.g., maintaining a flow in the bypass equivalent or near equivalent to the flow within the $CO_2$ sampling site, e.g., 200 cc/min) is desired. This prevents corruption of the $CO_2$ waveform and respiration rate calculations in the event one site became occluded such that the bypass and capnometer lines flowed at different rates.

Figure 6:
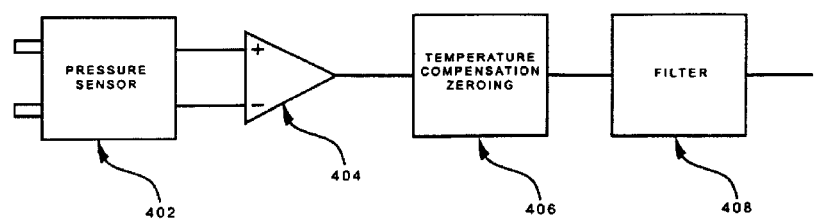
FIG. 6 is a schematic diagram of pressure transducer circuitry in one embodiment of the invention.

FIG. 6 shows a schematic of the electronic circuitry associated with pressure transducers 356 and 362. Such circuitry includes a pressure sensor 402, a hi-gain amplifier 404, a temperature compensating zeroing circuit 406 and a low pass filter 408. This gain and temperature zeroing circuitry ensure signal quality for the pressure transducers.

Figure 7:
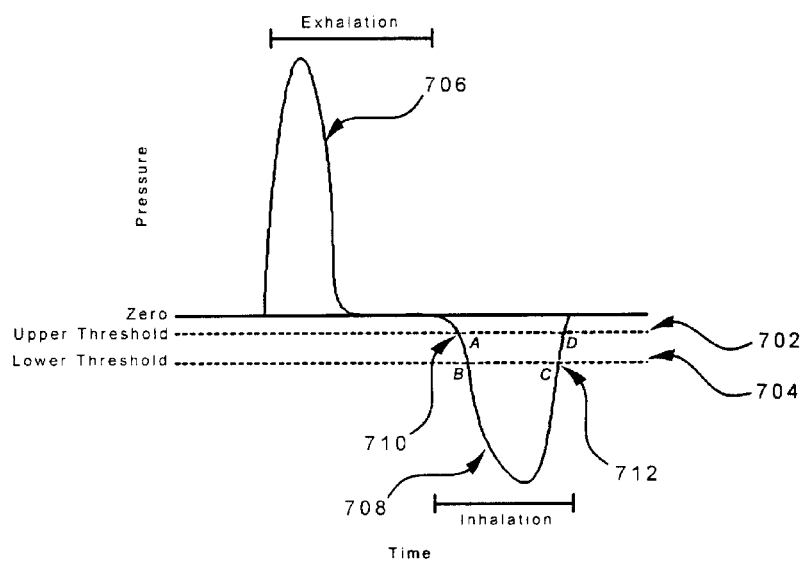
FIG. 7 is a diagram of the pressure wave form during a respiration cycle used in the method of the invention.

FIG. 7 is a diagram of the pressure reading (oral or nasal) during a typical respiration cycle with thresholds A, B, C and D identified in accordance with the preferred method of the invention. As is shown, as exhalation begins, the pressure becomes positive, eventually reaching a peak then dropping back to zero as the exhalation completes. The beginning of inhalation is indicated by the pressure becoming negative. The pressure will become more negative during the first portion of inhalation then trend back towards zero as inhalation ends.

The control software of the present invention defines an upper and a lower threshold value 702, 704, respectively. Both are slightly below zero, with the lower threshold 704 being more negative than the upper threshold 702. During each respiration cycle the software determines when the thresholds 702, 704 are crossed (points A, B, C, and D, FIG. 7) by comparing the pressures to one of the two thresholds. The crossings are expected to occur in sequence, i.e., first A, then B followed by C, and finally D. An $O_2$ source valve is turned up (e.g., to 10–15 liters/min of flow) when point A is reached and turned down (e.g., to 2–3 liters/min of flow) when C is reached, thus providing the highest oxygen flow during the majority of the inhalation phase.

Figure 8:
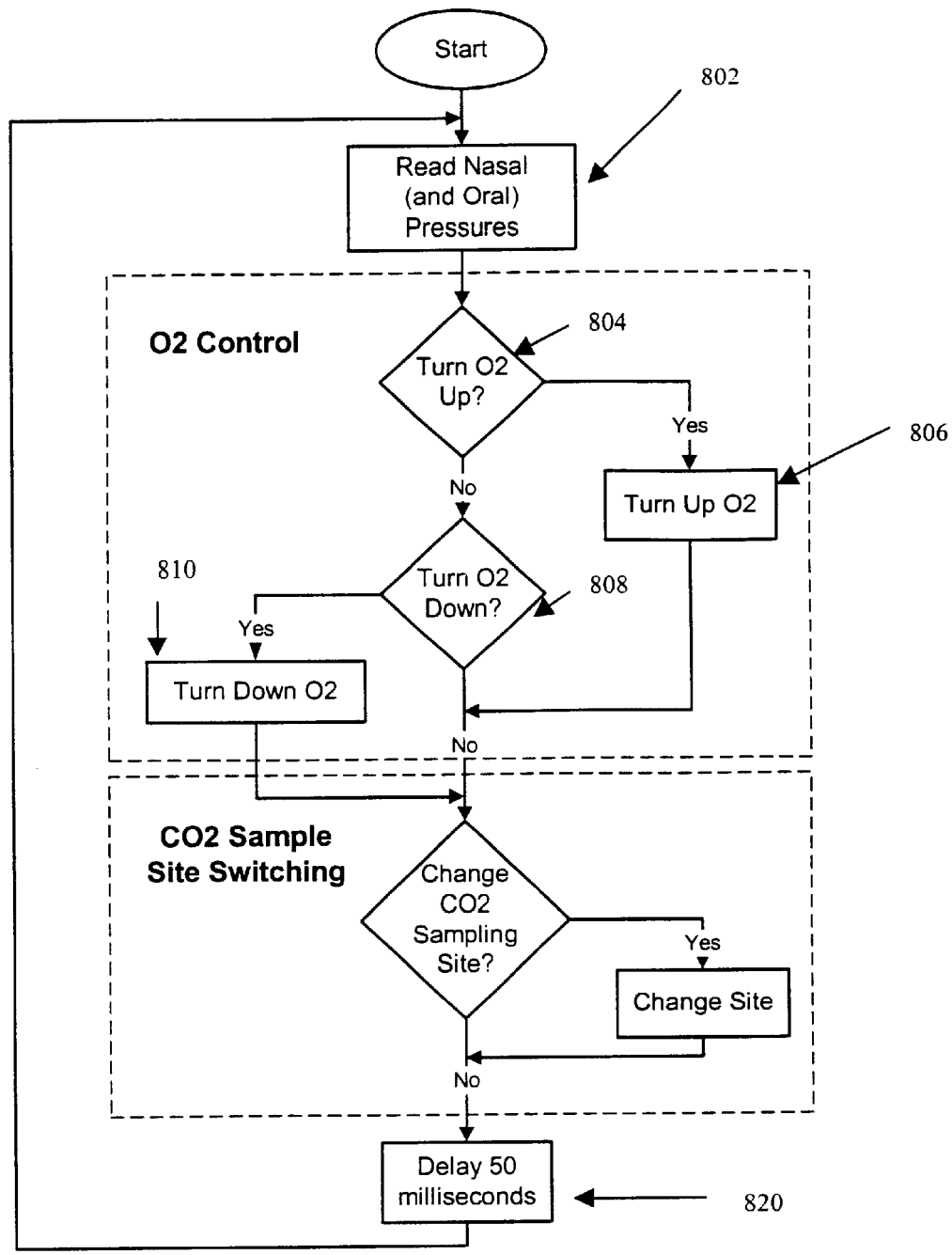
FIG. 8 is a flow chart of a preferred embodiment of the method of the invention.

To determine when the threshold crossings occur, the software examines the pressures from the oral and nasal pressure sensors at periodic intervals, e.g., at 50 milli/seconds (e, FIG. 8). During each examination the software combines the oral and nasal pressures then compares the combined pressure to one of the two thresholds as allows.

As shown by the flowchart of FIG. 8, when the software begins execution, it awaits a combined pressure value less than the upper threshold (point A). When this condition is met, the software turns up the $O_2$ valve to a higher desired flow (e.g., 10–15 liters/min) then begins looking for a pressure value less than the lower threshold (point B). When this occurs the software waits for a combined pressure value that is greater than the lower threshold (point C). When this value is read, the $O_2$ is turned down to the lower desired flow rate (e.g., 2–3 liters min) and the software awaits a pressure value that exceeds the upper threshold (point D). Once this value is read, the cycle begins again for the next breath.

As described above, a capnometer is used to provide information such as $EtCO_2$ and respiration rate by continually sampling the level of $CO_2$ at a single site. Since breathing can occur through the nose, mouth, or both, the software must activate valves 354 (FIG. 5), that switch the capnometer-sampling site to the source providing the best sample, i.e., mouth or nose.

As is also shown in FIG. 8, the software accomplishes this by examining the oral and nasal pressure readings at periodic intervals. During each examination, the current and prior three oral pressure values are compared to the corresponding nasal pressure values. If the combined nasal pressures exceed the combined oral pressures by more than a factor of three, the capnometer sample is obtained at the nose. If the combined oral pressures exceed the combined nasal pressures by more than a factor of three, the sampling occurs at the mouth.

The above-described system and method thus provides improved delivery of supplemental $O_2$ gas and ventilatory monitoring without use of a face mask. The system and method are particularly useful in medical environments where patients are conscious (thus comfort is a real factor) yet may be acutely ill, such as in hospital laboratories undergoing painful medical procedures, but also in the ICU, CCU, in ambulances or at home in for patient-controlled analgesia, among others. It should be understood that the above describes only a preferred embodiment of the invention and other equivalent embodiments are contemplated.

What is claimed is:

1. A method for supplying supplemental oxygen to a person, the method comprising the steps of: determining whether the person is in an exhalation or inhalation phase of a respiratory cycle; delivering a higher flow of oxygen to the person during the inhalation phase of the respiratory cycle; comparative sampling of nasal and oral gases for and monitoring the ventilation of the person in accordance with the determination of the person's primary respiratory site.

2. The method of claim 1 wherein the oxygen is delivered to the person in the area of the person's nose and mouth.

3. The method of claim 2, wherein said oxygen is delivered to the areas of the person's nose and mouth using a mask-free cannula.

4. The method of claim 1 wherein the determining of whether the person is in the exhalation or inhalation phase is accomplished by analyzing pressure in a breath airstream of the person.

5. The method of claim 4 wherein the pressure in the person's breath airstream is determined by individually sampling the pressure at a nasal respiratory site and an oral respiratory site of the person, and wherein said individual sampling is also used in said determining of said primary respiratory site.

6. The method of claim 1 wherein the determining of the person's primary respiratory site is accomplished by sampling pressures in or near a nasal respiratory site and an oral respiratory site of the person and comparing said pressures to determine a greater one of said pressures.

7. The method of claim 6, wherein said primary respiratory site demonstrates a greater pressure swing during said respiratory cycle.

8. The method of claim 1 wherein the monitoring of the ventilation is accomplished by measuring amounts of $CO_2$ in end tidal exhalation of the person.

9. The method of claim 8 wherein the measuring is conducted on a continuous basis.

10. The method of claim 1, further comprising setting a higher flow rate of supplemental oxygen and a lower flow rate of supplemental oxygen, said higher flow rate being delivered to the person during the inhalation phase of the respiratory cycle and said lower flow rate being delivered to the person during the exhalation phase of the respiratory cycle.

11. The method of claim 10, wherein the flow of oxygen is gradually increased from said lower flow rate until it reaches said higher flow rate, said gradual increase being triggered by the beginning of said inhalation phase.

12. An apparatus for delivering supplemental oxygen to a person comprising: an oxygen delivery device; at least one airway sampling device, said airway sampling device including a nasal sampling device adapted to sample pressure in or near a nasal airway of the person and an oral sampling device adapted to sample pressure in or near an oral airway of the person; a pressure analyzer connected to said airway sampling device and adapted to determine a phase of a respiratory cycle of the person; a pressure comparator connected to said oral sampling device and said nasal sampling device and adapted to determine a primary respiratory site of the person; and a controller coupled to said pressure analyzer; wherein the oxygen delivery device is operated by said controller to deliver a higher flow of oxygen to the person in accordance with the phase of the person's respiratory cycle.

13. The apparatus in accordance with claim 9 also comprising a ventilatory sampling device connected to a ventilatory monitor.

14. The apparatus of claim 13 wherein the ventilatory sampling device comprises a nasal ventilatory sampling device and an oral ventilatory sampling device and wherein the person's ventilation is monitored from the primary respiratory site.

15. An apparatus in accordance with claim 12 wherein the controller delivers a higher flow of oxygen only during the inhalation phase of the person's respiratory cycle.

16. The apparatus of claim 12, wherein said oxygen delivery device comprises a mask-free cannula having a diffuser grid for supplying oxygen proximate to the person's nose and mouth.

17. The apparatus of claim 12, wherein said oxygen delivery device comprises an oral collection chamber for collecting a volume of expired gases that the person has breathed orally.

18. The apparatus of claim 17, wherein said oral collection chamber is mounted to said oxygen delivery device such that it can be slid to accommodate proportions of the person's face.

19. The apparatus of claim 12, further comprising a microphone adapted to capture breathing sounds of the person that can be amplified for hearing by a care giver.

20. The apparatus of claim 12, wherein said oral and said nasal sampling devices each comprise a pair of lumens, the first of said lumens in each said pair comprising a pressure sampling lumen and the second of said lumens in each said pair comprising a ventilatory sampling lumen.

21. The apparatus of claim 20, wherein said lumens are slidably mounted to an oxygen delivery cannula.

22. The apparatus of claim 20, wherein gas sample bypass circuits maintain gas flow rates in said ventilatory sampling lumens if one of said ventilatory lumens becomes occluded or if gas within one of said ventilatory lumens is not being analyzed.

23. The apparatus of claim 22, wherein valves are employed to alternatively connect either of said ventilatory lumens to a gas analyzer under predetermined conditions.

24. The apparatus of claim 20, wherein said lumen pairs are mounted on a cannula, and wherein said controller is adapted to minimize entrainment of supplemental oxygen flow into said ventilatory sampling lumens.

25. The apparatus of claim 9, wherein said pressure analyzer and said pressure comparator comprise pressure transducers.

26. A method for mask-free delivery of supplemental oxygen to a patient, said method comprising:
sampling pressure at a nasal respiratory site;
sampling pressure at an oral respiratory site;
comparing said nasal respiratory site pressure and said oral respiratory site pressure to identify one of said sites as a primary respiratory site;
monitoring pressure changes at said respiratory sites to determine when said patient is inhaling; and
delivering a higher flow of oxygen proximate to said respiratory sites only whenever said patient is inhaling.

27. The method according to claim 26, further comprising monitoring ventilation of the patient by analyzing expired gases at the patient's primary respiratory site.

28. The method according to claim 26, wherein said steps of sampling pressures comprises determining pressure swings at each respiratory site, and wherein said step of comparing said pressures comprises identifying the site having the greater pressure swing as the primary respiratory site.

29. The method according to claim 26, wherein said primary respiratory site is switched to a new primary respiratory site whenever a preset number of consecutive pressure samples measured at another respiratory site exceeds corresponding pressure samples at said primary respiratory site by a preset multiple.

30. The method according to claim 29, wherein said series of consecutive pressure samples comprises at least four pressure samples in a row.

31. The method according to claim 29, wherein said preset multiple is 3.

32. The method according to claim 26, further comprising setting a higher flow rate of supplemental oxygen and a lower flow rate of supplemental oxygen, said higher flow rate being delivered when the patient is inhaling and said lower flow rate being delivered to the patient at other times.

33. The method according to claim 32, wherein a mask-free cannula is employed to deliver said oxygen and to sample pressure at said respiratory sites.

34. The method according to claim 32, wherein flow of oxygen proximate to said respiratory sites is gradually increased until it reaches said higher flow of oxygen, said gradual increase being triggered when the patient begins to inhale.

35. The method according to claim 26, wherein said nasal respiratory site pressure and said oral respiratory site pressure is added to calculate a total breath pressure, and wherein said total breath pressure is compared with an upper threshold pressure value and a lower threshold pressure value to control delivery of said oxygen during a respiratory cycle of the patient.

36. The method according to claim 35, wherein said higher flow of oxygen is delivered after said total breath pressure meets said upper threshold pressure value and is ceased after said total breath pressure meets said lower threshold pressure value.

37. A method for supplying supplemental oxygen to a person, the method comprising:
determining whether the person is exhaling or inhaling according to a breathing cycle;
automatedly identifying a primary respiratory site of the person;
altering a flow rate of supplemental oxygen being supplied to the person between a preset low flow rate and a preset high flow rate wherein said low flow rate is delivered to the person when exhaling and said high flow rate is delivered to the person when inhaling; and
monitoring ventilation of the person at said primary respiratory site in accordance with delivery of said flow rates.

38. The method according to claim 37, wherein said high flow rate of supplemental oxygen is delivered to the person through a delivery device having a plurality of small holes near respiratory sites of the patient so as to avoid discomfort resulting from an impact of high pressure oxygen.

39. The method according to claim 37, wherein said high flow rate of supplemental oxygen is delivered to the person through a delivery device having a plurality of small holes near respiratory sites of the patient so as to minimize entrained air.

40. The method according to claim 37, wherein oxygen is delivered to the person in the area of the person's nose and mouth.

41. The method according to claim 37, wherein the identifying of the person's primary respiratory site is accomplished by sampling pressures in nasal and oral respiratory sites of the person and comparing said pressures to determine a greater one of said pressures.

42. The method according to claim 41, wherein comparing said pressures to determine the greater pressure comprises identifying the site demonstrating a greater pressure swing as the primary respiratory site.

43. The method according to claim 37, wherein the determining of whether the person is in the exhalation or inhalation phase is accomplished by analyzing the pressure in the person's breath airstream.

44. The method according to claim 43, wherein the pressure in the person's breath airstream is determined by individually sampling pressure at nasal and oral respiratory sites and adding said oral and nasal pressures to calculate a breath airstream pressure.

45. The method according to claim 43, wherein said breath airstream pressure is compared with an upper and a lower pressure threshold wherein both of said thresholds are lower than ambient pressure.

46. The method according to claim 45, wherein said upper and lower thresholds serve as triggers for initiating delivery of said high and said low flow rate respectively.

47. The method according to claim 37, wherein said monitoring of the ventilation is accomplished by measuring carbon dioxide levels in exhaled gases of the person.

48. The method according to claim 47, wherein said measuring of the carbon dioxide levels is accomplished by measuring amounts of carbon dioxide in end-tidal exhalation of the person.

49. The method according to claim 37, wherein said monitoring step comprises measuring a concentration of carbon dioxide in expired gases when said person exhales.

* * * * *